United States Patent [19]

Weigele et al.

[11] 4,216,008
[45] Aug. 5, 1980

[54] BUTENOIC ACID DERIVATIVES

[75] Inventors: Manfred Weigele, North Caldwell; Dennis D. Keith, Montclair, both of N.J.

[73] Assignee: Hoffmann-La Roche Inc., Nutley, N.J.

[21] Appl. No.: 908,043

[22] Filed: May 22, 1978

Related U.S. Application Data

[63] Continuation of Ser. No. 653,697, Jan. 30, 1976, abandoned.

[51] Int. Cl.$^2$ ............... C07C 103/85; C07C 103/49; A01N 9/24
[52] U.S. Cl. .......................... 71/106; 560/39; 560/170; 71/111; 260/456 A; 548/228; 562/567
[58] Field of Search .................. 560/41, 170, 39; 71/106, 111

[56] References Cited

U.S. PATENT DOCUMENTS

| | | | |
|---|---|---|---|
| 2,476,443 | 7/1949 | Harris | 560/39 |
| 2,588,969 | 3/1952 | Dickey | 560/38 |
| 2,976,285 | 3/1961 | Gash | 560/168 |
| 3,949,000 | 4/1976 | Violet | 560/41 |

OTHER PUBLICATIONS

Clarke, "Chemistry of Penicillin", pp. 755, 825 & 826, (1949).
Galantay, J. Org. Chem., 28, pp. 98–102 (1963).

*Primary Examiner*—Norman Morgenstern
*Assistant Examiner*—Michael Shippen
*Attorney, Agent, or Firm*—Jon S. Saxe; Bernard S. Leon; Frank P. Hoffman

[57] ABSTRACT

The present invention is directed to compounds of the formula

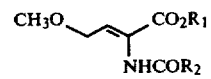

I wherein $R_1$ is lower alkyl and $R_2$ is lower alkyl or aryl. Also provided are methods for preparation of these compounds. The compounds of formula I above are useful as plant growth regulants.

6 Claims, No Drawings

BUTENOIC ACID DERIVATIVES

This is a continuation of application Ser. No. 653,697 filed Jan. 30, 1976, now abandoned.

DESCRIPTION OF THE INVENTION

The present invention relates to compounds of the formula

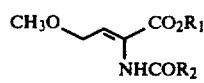

wherein $R_1$ is lower alkyl and $R_2$ is lower alkyl or aryl. The compounds of formula I exhibit activity as plant growth regulants.

As used throughout this disclosure, the term "lower alkyl" signifies straight or branched chain hydrocarbon groups containing from 1 to 7, preferably from 1 to 4, carbon atoms, such as methyl, ethyl, propyl and the like.

By the term "aryl" is meant—a substituted or unsubstituted aromatic moiety such as, phenyl. Suitable substituents of the aromatic moiety include halo, nitro, alkoxy, hydroxy and alkyl substituents.

Preferred among the compounds of formula I above are those wherein $R_1$ and $R_2$ signify lower alkyl of 1 to 4 carbon atoms, most preferably wherein $R_1$ and $R_2$ are methyl.

The compounds of formula I above may be prepared by several different methods of synthesis. The following reaction schemes are set forth to illustrate some of the general methods of synthesis of the compounds:

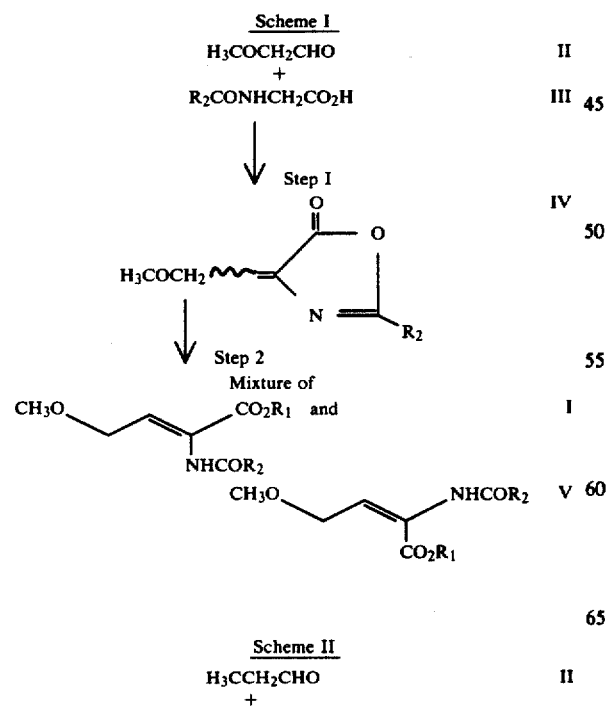

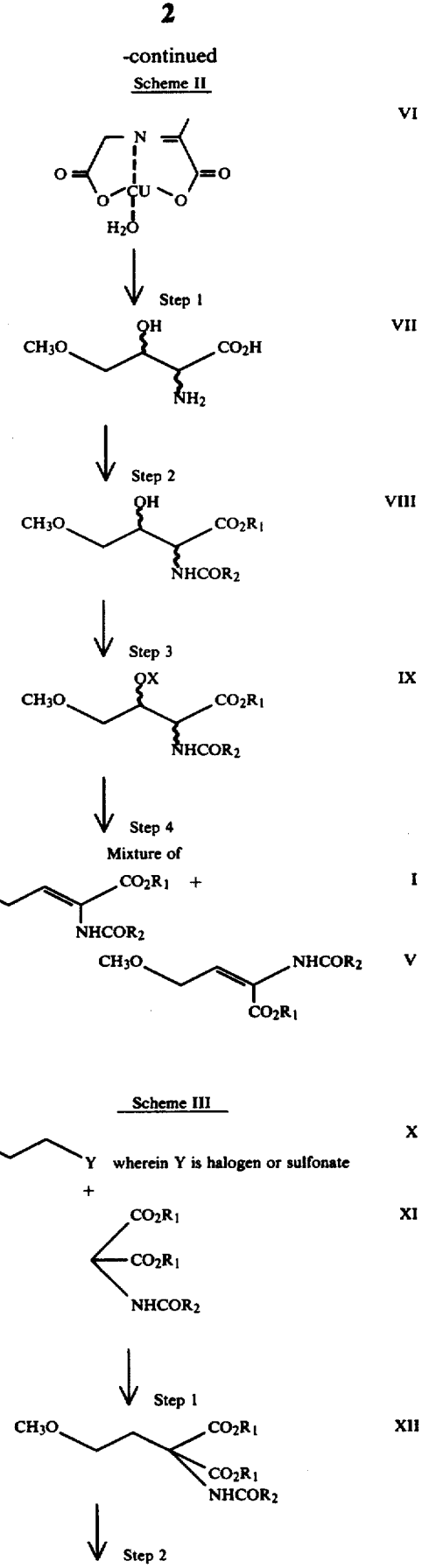

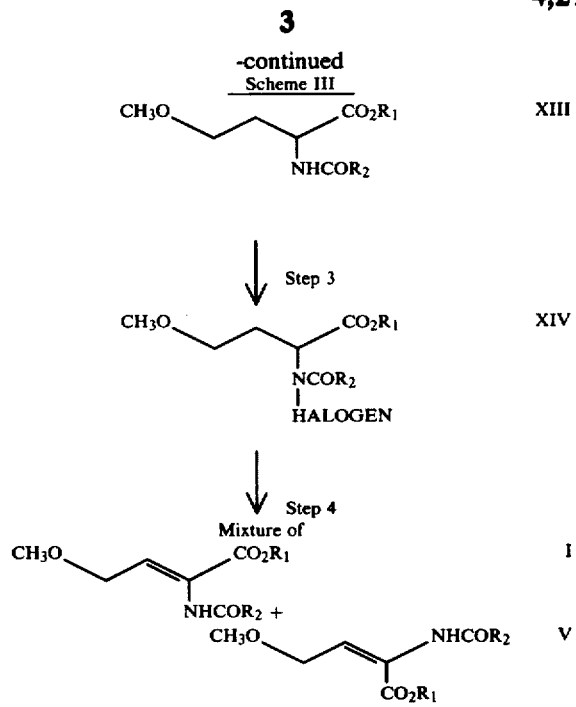

-continued
Scheme III

In the above reaction schemes $R_1$ is lower alkyl; $R_2$ is lower alkyl or aryl and X is alkyl sulfonyl or aryl sulfonyl, e.g., benzene sulfonyl, toluene sulfonyl or mesyl and the like.

SCHEME I, STEP I

An N-alkanoyl or N-aroyl glycine (III) e.g. an N-acylglycine such as N-acetyl glycine or N-benzoyl glycine is reacted with an aliphatic anhydride such as acetic anhydride preferably in the presence of an acetate salt buffer such as sodium acetate or lead diacetate. The reaction is carried out in an inert solvent such as tetrahydrofuran, dioxane or dimethoxyethane and the reaction allowed to proceed at from room temperature to reflux temperature for a period of about one hour although the length of time is not critical. To the reaction mixture is thereafter added methoxyacetaldehyde (II) and additional inert solvent as above and the mixture, with preferable heating, is stirred for about one to four hours. The product (formula IV) is thereafter filtered and isolated utilizing well known techniques.

SCHEME I, STEP II

The product of Step I is dissolved in an alkanol of the formula $R_1OH$, e.g., methanol, ethanol, propanol, etc., and thereafter treated with an alkali metal alkoxide (corresponding to the selected solvent), e.g., sodium or potassium methoxide, sodium or potassium ethoxide, etc., until the reaction mixture is slightly basic. The final product is thereafter isolated by suitable techniques as to yield a compound of formula I and as a minor by-product anisomeric compound of formula V.

SCHEME II, STEP I

A copper (II) salt of N-Pyruvylideneglycine (VI) in an aqueous alcoholic solvent is mixed with methoxyacetaldehyde (II). To the mixture is then added an alkali metal hydroxide, e.g., sodium or potassium hydroxide to adjust and maintain the mixture at about pH 9 for the required reaction time. Thereafter the product (VII) is isolated in any suitable manner to obtain the desired 4-methoxy threonine (VII).

SCHEME II, STEP II

The product of Step I is acylated by any well known method, e.g., by reaction with acetic anhydride or benzoyl chloride and the N-acylated product thereafter esterified, e.g., by treatment with a dialkyl sulfate, e.g., dimethylsulfate, in the presence of an aqueous base e.g., an alkali metal hydroxide for example sodium or potassium hydroxide. The desired product is thereafter isolated using any well known means to yield a compound of formula VIII.

SCHEME II, STEP III

The protected threonine derivative (VIII) is reacted with an alkyl sulfonyl chloride or aryl sulfonyl chloride, e.g., methane sulfonyl chloride or toluene sulfonyl chloride in the presence of a tertiary amine base, e.g., triethylamine or trimethylamine, at about 0° C. The sulfonate derivative (IX) is recovered utilizing well known prior art techniques.

SCHEME II, STEP IV

The sulfonate derivative (IX) is reacted with a secondary amine, e.g., diethylamine or dimethylamine in an inert solvent, e.g., methylene chloride, at an elevated temperature, i.e., above room temperature and sufficiently high to accomplish elimination of sulfonic acid. The end product (I) and its geometric isomer as by product (V) were thereafter isolated and separated by suitable techniques.

SCHEME III, STEP I

A reactive 2-methoxy ethyl compound (X) such as a 2-methoxy ethyl halide e.g., bromide or chloride, or a sulfonate derivative of 2-methoxy ethanol is allowed to react with an akali metal salt, e.g., sodium or potassium salt of a dialkyl N-acylaminomalonate (XI) to give as a final product a dialkyl acylamino(2-methoxyethyl)malonate (XII).

SCHEME III, STEP II

The malonate (XII) is thereafter subjected to alkaline hydrolysis followed by in situ acidification, thermal decarboxylation and reesterification to produce a compound of formula XIII. The above techniques are well known to one skilled in the art and the selection of particular technique conditions should be dictated by the nature of the starting material (XII) and the resultant intermediate products.

SCHEME III, STEP III

A compound of formula XIII is treated with a solution of active halogen, e.g., tertiary butyl hypochlorite, elemental chlorine bromine, etc., to accomplish formation of the N-halo compound of formula XIV. The solvent selected is not critical as long as it is compatible with the reactants present in the mixture. Temperature, although it is not critical, should be maintained at about 5°-10° C. for optimum results. After removal of the initial solvent, isolation of a solution containing formula XIV compound was achieved by standard extraction techniques utilizing an inert solvent, e.g., a halogenated hydrocarbon, and being careful that the temperature does not exceed 30°-40° C. Another criteria for selection of the extraction solvent should be its compatibility for the subsequent reaction step.

SCHEME III, STEP IV

The isolated solution, e.g., compound of formula XIV in a halogenated hydrocarbon solvent, is subjected to dehydrohalogenation by treatment with a strong organic base such as a tertiary amine base, e.g., 1,4-diazabicyclo[2.2.2] octane, or a cyclic amidine, base, e.g., 1,5-diazabicyclo[5.4.0]undec-5-ene. The compound of formula I and its formula V by-product are thereafter recovered and separated by standard techniques.

The compounds of the present invention may be incorporated into compositions which may be applied to the plants which are to be treated. In order to effect uniform distribution of the active compound of the growth regulating compositions according to this invention, the compound can be mixed with agriculturally acceptable adjuvants conventionally used for such applications so that they may be formulated as solutions, emulsions, dispersions, dusts or wettable powders.

The term "agriculturally acceptable adjuvant" as used herein includes:

(a) agriculturally acceptable inert carrier materials as, for example, surface active agents, carriers, sticking agents, stabilizers, filler, modifiers, diluents, conditioning agents and the like and (b) other active agricultural materials such as herbicides, fungicides, insecticides, or plant growth regulants which complement the active plant growth regulant ingredient or extend the useful life of the composition.

It is understood, of course, that the adjuvant added to the compositions of this invention comprises either only the inert materials of (a), the active materials of (b) or a combination of materials from (a) and (b).

Liquid formulations of the active compounds for direct spraying may be made, for example, as aqueous formulations where possible or as formulations in solvent mixtures containing acetone, methanol or ethanol.

Emulsions can be prepared containing 25–50% of the active ingredient, and surface active agents, e.g., wetting agents, dispersing agents, emulsifying agents and the like, in sufficient amounts to impart the desired characteristics to the formulation.

For use in the above formulations, a wettable powder premix for preparing the aqueous solutions or emulsions may be prepared. The powder premix may contain, besides the active ingredient, a surface active agent such as Tween 20 ® or Etalfix ®.

Also within the ambit of the present invention are the novel compounds of formulas IV, VII, VIII, IX, and XIV which are useful as intermediates to produce the novel plant growth regulant compounds of formula I.

The following examples are illustrative and not limitative of the present invention. All temperatures are given in degrees centigrade.

EXAMPLE 1

4-(2-Methoxyethylidene)-2-methyl-5-oxazolone

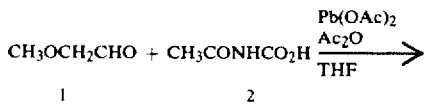

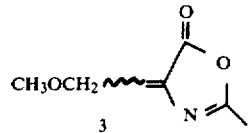

A flask equipped with a mechanical stirrer, reflux condenser, dropping funnel, and drying tube was charged with 38.5 g (0.33 mol) of N-acetylglycine (2), 134 g (1.3 mol) of acetic anhydride, 54 g (0.166 mol) of lead acetate, and 450 ml of tetrahydrofuran (THF). The mixture was heated with stirring at reflux temperature for 1 hr. A solution consisting of 37 g (0.5 mol) of methoxyacetaldehyde (1) and 220 ml of THF was then added dropwise over a 2½ hr period. The resultant mixture was heated with stirring at reflux temperature for an additional 4 hrs. The reaction was allowed to cool, diluted with 1 l. of ether, and filtered through a pad of Celite ®. The filtrate was concentrated in vacuo and the dark brown fluid residue was distilled under reduced pressure. The fraction boiling at 60°–83°/0.5 mm consisted mainly of 4-(2-methoxyethylidene)-2-methyl-5-oxazolone (3): NMR (CDCl₃) δ 6.5 (m, 1H, —CH₂CH=), 4.35 (m, 2H, —CH₂CH—), 3.3 (s, 3H, CH₃O—), 2.2

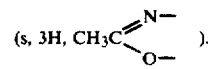

EXAMPLE 2

Z-2-Acetamido-4-methoxy-2-butenoic acid Methyl Ester (4) and E-2-Acetamido-4-methoxy-2-butenoic acid Methyl Ester (5)

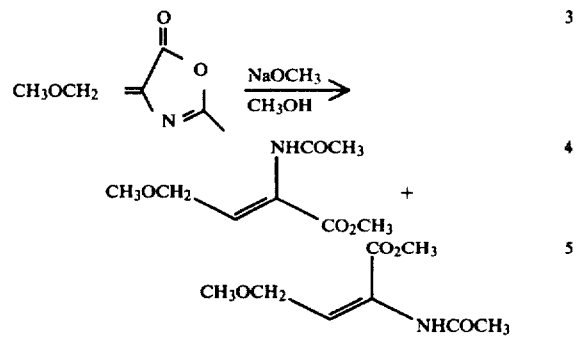

A solution consisting of 19 g (0.165 mol) of oxazolones 3 and 100 ml of methanol was treated with solid sodium methoxide until the reaction mixture was slightly basic (pH 9 as indicated by moist pH paper). The solution was stirred for ¾ hr. at room temperature. The reaction mixture was concentrated in vacuo, and the residue taken up in 500 ml of ether. Petroleum ether (bp 35°–60°) was added until the solution was slightly turbid. An additional portion of ether was added to clear the turbidity and the resultant solution was treated with charcoal and filtered through Celite ®. The solvents were removed in vacuo, and the residue dried at 0.1 mm. Crystallization from ether/petroleum ether (bp 35°–60°) yielded Z-2-acetamido-4-methoxy-2-butenoic acid methyl ester (4): mp 60°–61°; IR (CHCl₃) 3415, 1720, 1700, 1500 cm⁻¹; UV (EtOH) λmax 226 nm (ϵ7500); NMR (CDCl₃) δ 7.5 (broad, 1H, N$\underline{H}$), 6.7 (t, 1H, —CH₂C$\underline{H}$=), 4.1 (d, 2H, —C$\underline{H}_2$CH=), 3.8 (s, 3H, C$\underline{H}_3$O₂C—), 3.4 (s, 3H, C$\underline{H}_3$OCH₂—), 2.14 (s, 3H, C$\underline{H}_3$CONH—). (Calcd. for C₈H₁₃NO₄: C, 51.33; H, 7.00; N, 7.48. Found: C, 51.20; H, 7.13; N, 7.69.)

The mother liquors from the crystallization of 4 were concentrated in vacuo to yield an oil which contained some 4 but consisted mainly of E-2-acetamido-4-methoxy-2-butenoic acid methyl ester (5): NMR (CDCl₃) 7.3 (broad, 1H, N$\underline{H}$), 7.1 (t, 1H, —CH₂C$\underline{H}$=), 4.3 (d, 2H, —C$\underline{H}_2$CH=), 3.7 (s, 3H, C$\underline{H}_3$O₂C—); 3.3 (s, 3H, C$\underline{H}_3$OCH₂—), 2.0 (s, 3H, C$\underline{H}_3$CONH—).

EXAMPLE 3

2-Amino-3-hydroxy-4-methoxybutanoic acid (7)

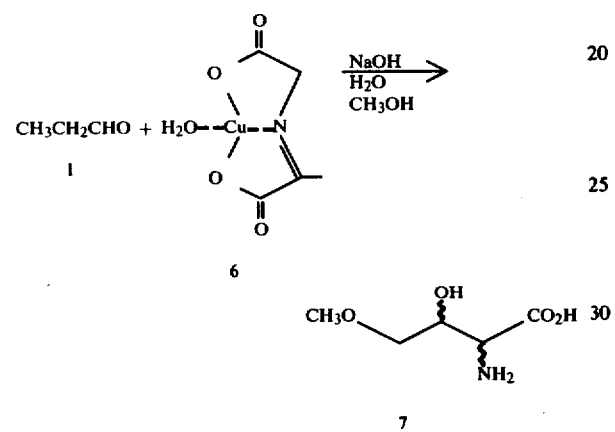

N-Pyruvylideneglycinatoaquo copper (II) dihydrate (6, 60 g., 0.23 mol)¹ was suspended in 1 l. of water/methanol (2:1), and the resultant mixture cooled with an ice bath. Methoxyacetaldehyde (1, 42 g., 0.568 mol) was added to the suspension. The resultant mixture was treated dropwise over a period of 1 hr. with 190 ml of 1 N sodium hydroxide. The suspension at first became very thick and then dissolved during the addition. The pH of the resultant solution was 9. After stirring for 1 hr at room temperature, another 20 ml of 1 N sodium hydroxide was added, and the solution was allowed to stand 1¼ hrs. At this time, another 10 ml of 1 N sodium hydroxide was added. After standing an additional hr, the pH was adjusted to 4.5 with 3 N acetic acid (approx. 100 ml). Hydrogen sulfide was bubbled through the solution until no more CuS precipitated. The mixture was filtered through a pad of Celite ®, and the filtrate concentrated in vacuo to approximately 400 ml. This solution was applied to an ion exchange column (AG$^R$ 50W-X4; 100–200 mesh; H⁺ form; 900 ml). The column was washed with water (3 l.), methanol (2 l.), and water (1 l.). The amino acid was eluted with 500 ml of 1 N ammonium hydroxide. The fraction containing the amino acid was concentrated in vacuo to yield 2-amino-3-hydroxy-4-methoxybutenoic acid (7) as white crystals. One of the diastereomers was obtained by crystallization from water/ethanol: mp 186°–187°; NMR (D₂O) δ4.8 (m, 1H, —C$\underline{H_2}$CH>), 4.3 (d, 1H, C$\underline{H}$-N), 4.1 (d, 2H, —C$\underline{H_2}$CH>), 3.9 (s, 3H, C$\underline{H}_3$O—).

¹T. Ichikawa, S. Maeda, T. Okamoto, Y. Araki and Y. Ishido, *Bull. Chem. Soc. Japan*, 44, 2779 (1971).

EXAMPLE 4

2-Acetamido-3-hydroxy-4-methoxybutenoic acid Methyl Ester

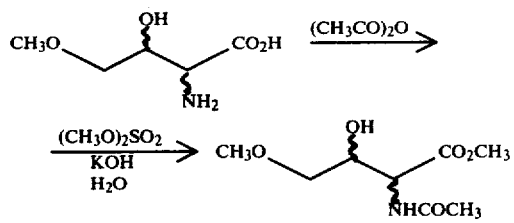

To a solution of amino acid 7 (34 g, 0.23 mol) in 300 ml of water cooled to 0° was added dropwise with stirring, 10 ml of acetic anhydride. After 1 hr, an additional 10 ml of acetic anhydride was added. The process was continued until a total of 35 ml of acetic anhydride had been added. The reaction mixture was allowed to stand at 0° for 3 hrs. The solvent was then removed in vacuo at 50°. Water was added to the residue and after a homogeneous solution was obtained, the water was removed in vacuo at 50°. The addition and removal of water was repeated 3 more times. The resultant residue was subjected two more times to the entire sequence beginning with the addition of 35 ml of acetic anhydride in portions. The residue resulting from this treatment was dried in vacuo (0.1 mm) for 48 hr yielding 2-Acetamido-3-hydroxy-4-methoxybutanoic acid as a glass. This material was used directly in the next step.

The crude carboxylic acid was dissolved in 250 ml of water and the solution neutralized (pH 7 as indicated by pH paper) in 1 N KOH. Dimethylsulfate (30 ml) was added and the resultant two phase system was stirred vigorously for 2¼ hrs. During this time, the pH was maintained at approximately 7 by the periodic addition of saturated sodium bicarbonate solution. The temperature was then brought to 60° for 45 min and solid sodium bicarbonate was added in order to maintain pH 7. The reaction mixture was cooled, saturated with sodium chloride, and extracted 3 times with chloroform (250 ml). The extracts were dried over anhydrous sodium sulfate and concentrated in vacuo yielding 2-acetamido-3-hydroxy-4-methoxybutanoic acid methyl ester (8) as a beige solid. Crystallization from methylene chloride/petroleum ether (bp 35°–60°) gave one of the diastereomers as a white solid: mp 131°–134.5°; IR (CHCl₃) 3580, 3442, 1750, 1680, 1509, 1125 cm⁻¹; NMR (CDCl₃) δ6.5 (broad, 1H, N$\underline{H}$), 4.7 (m, 1H, C$\underline{H}$NH), 4.3 (m, 1H, CH₂C$\underline{H}$), 3.7 (s, 3H, C$\underline{H}_3$O₂C—), 3.3 (singlet superimposed on a multiplet, 6H, C$\underline{H}_3$OC$\underline{H}_2$—and $\underline{H}$O—), 2.0 (s, 3H, C$\underline{H}_3$CONH—). (Calcd. for C₈H₁₅NO₅: C, 46.82; H, 7.37; N, 6.83. Found: C, 47.03; H, 7.48; N, 6.85).

EXAMPLE 5

2-Acetamido-3-mesyloxy-4-methoxybutanoic Acid Methyl Ester (9)

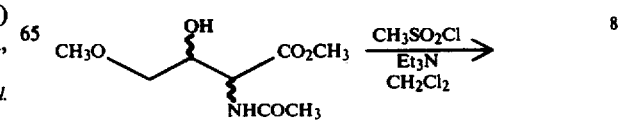

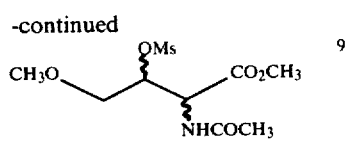

A solution consisting of 20.5 g (0.1 mol) of alcohol 8, 1 l of methylene chloride, and 20.5 ml of triethylamine was cooled to 0° under an argon atmosphere. Methanesulfonyl chloride (8.5 ml) was added dropwise with stirring. The resultant solution was maintained at 0° for ½ hr. Methanol (0.4 ml) was added, and the solvent was removed in vacuo (35°). The white solid residue was triturated with ethyl acetate and the extract filtered through a column containing silica gel (200 g). The fractions containing product (as determined by thin layer chromatography) were concentrated in vacuo yielding 2-acetamido-3-mesyloxy-4-methoxy-butenoic acid methyl ester (9) as a partially crystalline residue. Crystallization from ethyl acetate/petroleum ether (bp 35°–60°) gave one of the diastereomers as a white crystalline solid: mp 101.5°–104.5°; NMR (CDCl$_3$) δ 6.4 (broad d, 1H, N$\underline{H}$), 5.2 (m, 1H, CH$_2$C$\underline{H}$), 5.0 (m, 1H, C$\underline{H}$NH), 3.8 (s, 3H, C$\underline{H}_3$O$_2$C—), 3.6 (m, 2H, CH$_3$OC$\underline{H}_2$—), 3.3 (s, 3H, C$\underline{H}_3$OCH$_2$—), 3.0 (s, 3H, C$\underline{H}_3$SO$_3$—), 2.0 (s, 3H, C$\underline{H}_3$CONH—). (Calcd. for C$_9$H$_{17}$NO$_7$S: C, 38.16; H, 6.05; N, 4.94; S, 11.31. Found: C, 38.34; H, 6.21; N, 4.92; S, 11.27).

EXAMPLE 6

Z-2-Acetamido-4-methoxy-2-butenoic Acid Methyl Ester (4) and E-2-Acetamido-4-methoxy-2-butenoic Acid Methyl Ester (5)

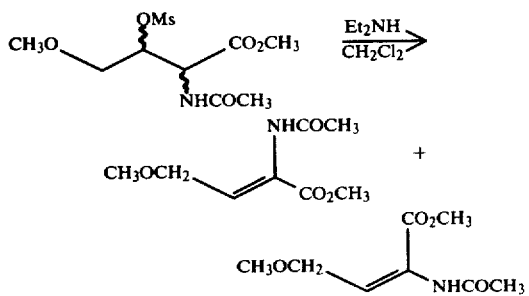

A solution consisting of 27.6 g (0.098 mol) of mesylate 9, 20.5 ml of diethylamine and 250 ml of methylene chloride was heated at reflux temperature for 2 hrs under an atmosphere of argon. The resultant solution was cooled, concentrated in vacuo and the residue filtered through a column of silica gel (125 g) using ethyl acetate as the eluent. The fractions containing product (as determined by thin layer chromatography) were combined and concentrated in vacuo. Crystallization of the residue from ether/petroleum ether (bp 35°–60°) yielded Z-2-acetamido-4-methoxy-2-butenoic acid methyl ester (4) identical to the material obtained by the previous method (Examples 1 and 2). The mother liquors from the crystallization of 4 were concentrated in vacuo to yield an oil which contained a 1:1 mixture of 4 and E-2-acetamido-4-methoxy-2-butenoic acid methyl ester (5).

EXAMPLE 7

Diethyl acetamido(2-methoxyethyl)malonate (12)

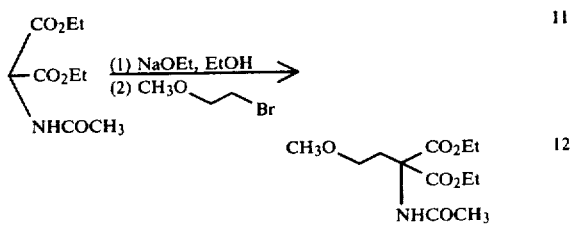

Sodium (34.9 g, 1.52 mol) was dissolved in 750 ml of dry ethanol (distilled from magnesium ethoxide). To this solution was added 330 g (1.52 mol) of powdered diethylacetamido malonate (11). After the addition of another 250 ml of dry ethanol, the reaction mixture was stirred at room temperature for ½ hr. To the resultant cloudy suspension was added 250 g (1.8 mol) of 2-methoxyethyl bromide. The resulting mixture was then heated with stirring at reflux temperature for 22 hrs. The solvent was removed in vacuo (40°–45°/20 mm) and the residue taken up in 1 l. of methylene chloride. The resultant suspension was filtered through a sintered glass funnel, and the filtrate was neutralized (as indicated by moist pH paper) with acetic acid, washed with saturated sodium chloride solution (250 ml), with saturated sodium bicarbonate solution (500 ml), and lastly with another portion of saturated sodium chloride solution (300 ml). The organic layer was then dried over anhydrous sodium sulfate and concentrated in vacuo (40°/20 mm). The last traces of solvent were removed at 0.1 mm. The material could be further purified by distillation yielding diethyl acetamido(2-methoxyethyl)-malonate (12): bp 140°–145°/0.2 mm; IR (CDCl$_3$) 3410, 1735, 1688, 1490 cm$^{-1}$; NMR (CDCl$_3$) 6.9 (broad, 1H, N$\underline{H}$), 4.2 (q, 4H, 2 CH$_3$C$\underline{H}_2$O—), 3.4 (m, 2H, CH$_3$OCH$_2$—), 3.2 (s, 3H, C$\underline{H}_3$OCH$_2$—), 2.6 (t, 2H, —OCH$_2$CH$_2$—), 2.0 (s, 3H, CH$_3$CONH—), 1.3 (t, 6H, 2 C$\underline{H}_3$CH$_2$O—). (Calcd. for C$_{12}$H$_{21}$NO$_6$: C, 52.35; H, 7.69; N, 5.09. Found: C, 52.16; H, 7.58; N, 4.95).

EXAMPLE 8

2-Acetamido-4-methoxybutanoic Acid Methyl Ester (13)

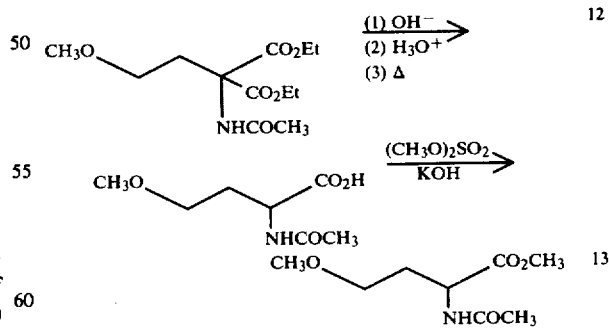

Acetamido malonate 12 (368 g, 1.34 mol) was added to 1.85 l. of 2 N sodium hydroxide. The mixture was stirred at room temperature for ½ hr, and then at reflux temperature for 1 hr. The resultant solution was cooled to 0° and brought to pH 3 (as indicated by pH paper) with 4 N hydrochloric acid (ca. 400 ml). The acidified solution was then slowly warmed to reflux temperature. The solution was maintained at reflux for 2 hrs, allowed to cool, and the solvent removed in vacuo 50°–55°/15 mm) yielding a mixture of 2-acetamido-4-methoxybutenoic acid and sodium salts.

The pH of the crude mixture was adjusted to 7 with 1 N potassium hydroxide (ca. 400 ml). At this point there remained a solid residue which was solubilized with water (ca. 400 ml). Dimethyl sulfate (125 ml) was added to the aqueous solution and the resultant mixture was stirred at room temperature for ½ hr. Another 125 ml of dimethyl sulfate was added dropwise. After the addition was complete, the pH of the reaction mixture was adjusted to 7 by the addition of solid sodium bicarbonate. The solution was stirred 1½ hrs and another portion of dimethyl sulfate (90 ml) was added. The pH was again adjusted to 7 with sodium bicarbonate. The solution was then warmed to 60° and more sodium bicarbonate added until the pH remained constant at 7. The reaction mixture was concentrated in vacuo to ca. 900 ml and extracted with three 1 l. portions of chloroform. The extracts were dried over anhydrous sodium sulfate and concentrated in vacuo yielding a brown oil. The oil was dissolved in ether and the solution treated with charcoal, followed by filtration through a pad of Celite ®. Concentration of the filtrate, followed by crystallization from ether/petroleum ether (bp 30°–65°) gave 2-acetamido-4-methoxybutenoic acid methyl ester (13) mp 61°–63°; IR (CHCl$_3$) 3430, 1745, 1650, 1510 cm$^{-1}$; NMR (CDCl$_3$) 6.5 (broad, 1H, N$\underline{H}$), 4.6 (m, 1H, C$\underline{H}$NH), 3.7 (s, 3H, C$\underline{H}_3$O$_2$C—), 3.4 (t, 2H, —OC$\underline{H}_2$C$\underline{H}_2$—), 3.3 (s, 3H, C$\underline{H}_3$OCH$_2$—), 2.04 (m, 2H, —OCH$_2$C$\underline{H}_2$—), 1.99 (s, 3H, C$\underline{H}_3$CONH—). (Calcd. for C$_8$H$_{15}$NO$_4$: C, 50.78; H, 7.99; N, 7.40. Found: C, 51.05; H, 7.78; N, 7.36).

EXAMPLE 9

Z-2-Acetamido-4-methoxy-2-butenoic Acid Methyl Ester (4) and E-2-Acetamido-4-methoxybutenoic Acid Methyl Ester (5)

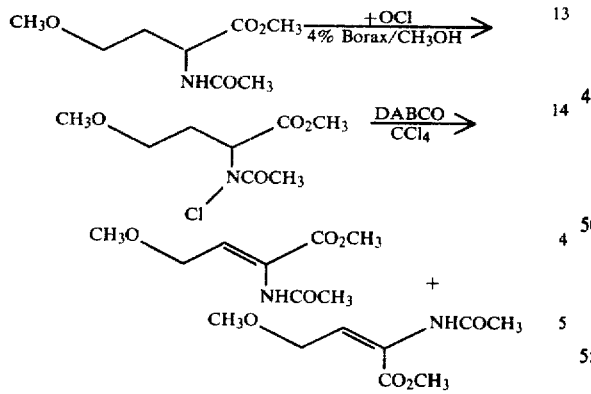

A solution consistin of 125 g (0.66 mol) of acetamide 13, 20 g of Na$_2$B$_4$O$_7$. 10 H$_2$O (Borax) and 500 ml of methanol was cooled to 0° and 160 ml of t-butyl hypochlorite was added dropwise to the solution. The addition and subsequent procedures were carried out in the dark. The temperature of the reaction mixture was kept between 5° and 10° during the addition by external cooling. After the addition was complete, the solution was allowed to warm to room temperature. After 1 hr at room temperature, the solvent was then removed in vacuo (30°/20 mm). The residue was further dried at 0.1 mm and then triturated with carbon tetrachloride (1 l.). The carbon tetrachloride solution was dried with anhydrous sodium sulfate and filtered yielding a clear colorless solution. Concentration of a small portion of the solution yielded N-chloroamide 14 as a colorless oil: NMR (CDCl$_3$) 5.3 (m, 1H, —CH$_2$C$\underline{H}$N), 3.8 (s, 3H, C$\underline{H}_3$O$_2$C—), 3.4 (m, 2H, CH$_3$OC$\underline{H}_2$), 3.3 (s, 3H, C$\underline{H}_3$OCH$_2$—), 2.3 (s, 3H, C$\underline{H}_3$CONCl—), 2.2 (m, 2H, —OCH$_2$C$\underline{H}_2$—).

The carbon tetrachloride solution was cooled by an ice bath to 0° under an atmosphere of argon. Powdered 1,4-diazabicyclo [2.2.2] octane (81 g, 0.72 mol) was added in portions at a rate so that the temperature did not exceed 30°. After the addition was complete, the ice bath was removed and the opaque mixture kept at room temperature for 15 hrs. The mixture was then filtered and the filtrate concentrated in vacuo. The residue was filtered through a column of silica gel (250 g) with ethyl acetate. The fractions containing the product (as indicated by thin layer chromatography) were concentrated in vacuo. Crystallization of the residue from ether/petroleum ether (bp 35°–60°) yielded Z-2-acetamido-4-methoxybutenoic acid methyl ester (4), identical to the material obtained by the previous methods (Examples 1 and 2, and Examples 3, 4, 5 and 6). The mother liquors from the crystallization were concentrated in vacuo to yield an oil which contained a 1:1 mixture of 4 and E-2-acetamido-4-methoxy-2-butenoic acid methyl ester (5).

TABLE 1

Triticum Weight Test

The purpose of this test is to detect promotion or retardation of shoot growth.

The species used was *Triticum aestivum* "Svenno" (wheat). Z-2-Acetamido-4-methoxy-2-butenoic acid methyl ester (4) was dissolved at 2% in acetone containing 1% of a wetting agent/emulsifier; this solution was diluted immediately before use with an equal amount of water.

Eleven seeds were sown in 450 ml plastic breakers containing a suitable soil mixture. Seeds were sown 3 cm deep. Two replications were made; in each pot the number of seedlings was reduced in two steps to 9 per pot. The plants were grown in the greenhouse for 12 days in Summer and 19 days in Winter (to have plants with 2 internodes) before treatment. The plants were sprayed with dispersions of the test compounds in acetone and water. After spraying, the plants were placed in the greenhouse. When necessary, natural daylight was supplemented by mercury vapour lamps to make a 16 hour long day. For each dosage, two replications (pots) were used.

Growth regulatory activity is assessed 15 days after treatment in Summer and 22 days after treatment in Winter.

At 1 kg per hectare, 4 increased fresh weight by 105%.

TABLE 2

Solanum Lycopersicum Fruit Test

The purpose of this test is to detect increase or decrease of fruit number. The species used was *Solanum lycopersicum*.

Z-2-Acetamido-4-methoxy-2-butenoic acid methyl ester (4) was dissolved at 2% in acetone containing 1% of a wetting agent/emulsifier; this solution was diluted immediately before use with an equal amount of water.

The seeds were sown 0.5 cm deep in a tray and transplanted 14 days later into 450 ml plastic beakers containing a suitable soil mixture. The plants were grown in the greenhouse for 34–42 days (first growth stage) before application. The plants were sprayed with dispersions of the test compounds in acetone and water. Afterwards, the plants were again placed in the greenhouse. When necessary, natural daylight was supplemented by mercury vapour lamps to make a 16 hour day. Three replications were used for each dosage.

Growth regulatory activity is assessed 50–60 days after treatment.

At 4 kg. per hectare, 4 caused a 115% increase in the number of fruits and a 365% increase in the number of flowers.

At 1 kg. per hectare, 4 caused a 230% increase in the number of flowers.

TABLE 3

Hordeum Weight—Increase Test

The purpose of this test is to detect promotion or retardation of shoot growth.

The species used was *Hordeum distichon* "Union" (Barley). Z-2-Acetamido-4-methoxy-2-butenoic acid methyl ester (4) was dissolved at 2% in acetone containing 1% of a wetting agent/emulsifier; this solution was diluted immediately before use with an equal amount of water.

Eleven seeds were sown in 450 ml plastic beakers containing a suitable soil mixture. Seeds were sown 1 cm deep. Two replications were made; in each pot the number of seedlings was reduced in two steps to 0 per pot. The plants were grown in the greenhouse for 12 days in Summer and 19 days in Winter (to have plants with 2 internodes) before treatment. The plants were sprayed with dispersions of 4 in acetone and water formulations. After spraying, the plants were placed in the greenhouse. When necessary, natural daylight was supplemented by mercury vapour lamps to make a 16 hour long day. For each dosage, 2 replications (pots) were used.

Growth regulatory activity is assessed 15 days after treatment in Summer and 22 days after treatment in Winter.

At 4 kg. per hectare, 4 increased the fresh weight by 115%.

At 1 kg. per hectare, 4 increased the fresh weight by 135%.

What is claimed:

1. A compound of the formula

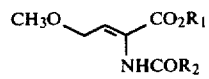

wherein $R_1$ is lower alkyl and $R_2$ is selected from the group consisting of lower alkyl and aryl.

2. A compound according to claim 1 wherein $R_1$ is lower alkyl and $R_2$ is lower alkyl.

3. A compound according to claim 2 wherein $R_1$ is methyl and $R_2$ is methyl.

4. The compound 2-acetamido-4-methoxy-2-butenoic acid methyl ester.

5. A plant growth stimulating composition comprising agriculturally acceptable adjuvants and as the active ingredient, an amount effective in stimulating plant growth of a compound of the formula

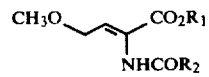

wherein $R_1$ is lower alkyl and $R_2$ is selected from the group consisting of lower alkyl and aryl.

6. The composition of claim 5 wherein $R_1$ is methyl and $R_2$ is methyl.

* * * * *